United States Patent [19]
Hayward et al.

[11] Patent Number: 6,162,440
[45] Date of Patent: *Dec. 19, 2000

[54] EBNA2 PEPTIDES AND METHODS OF USING SAME

[75] Inventors: S. Diane Hayward, Baltimore, Md.; Paul Dalling Ling, Sugarland, Tex.

[73] Assignee: Johns Hopkins University School of Medicine, Baltimore, Md.

[21] Appl. No.: 09/133,341

[22] Filed: Aug. 13, 1998

Related U.S. Application Data

[63] Continuation of application No. PCT/US97/02243, Feb. 12, 1997.
[60] Provisional application No. 60/011,557, Feb. 13, 1996.
[51] Int. Cl.[7] .......................... A61K 39/245; A61K 39/12
[52] U.S. Cl. ...................... 424/230.1; 424/204.1; 424/186.1; 424/199.1; 435/235.1; 435/325; 435/320.1; 435/5; 435/7.93; 514/13; 530/233; 536/23.72
[58] Field of Search .............................. 424/230.1, 204.1, 424/186.1, 199.1; 435/235.1, 325, 7.93, 5, 320.1; 514/13; 530/233; 536/23.72

[56] References Cited

FOREIGN PATENT DOCUMENTS

WO 95/32307  11/1995  WIPO .

OTHER PUBLICATIONS

Grossman et al., "The Epstein–Barr Virus Nuclear Antigen 2 Transactivator is Directed to Response Elements by the JK Recombination Signal Binding Protein," *Proc. Natl. Acad. Sci.*, vol. 91, No. 16, pp. 7568–7572 (1994).

Henkel et al., "Mediation of Epstein–Barr Virus EBNA2 Transactivation by Recombination Signal–Binding Protein JK," *Science*, vol. 265, pp. 92–95 (1994).

Ling et al., "The Epstein–Barr Virus Immortalizating Protein EBNA–2 is Targeted to DNA by a Cellular Enhancer–Binding Protein," *Proc. Natl. Acad. Sci.*, vol. 90, No. 20, pp. 9237–9241 (1993).

Ling et al., "Contribution of Conserved Amino Acids in Mediating the Interaction Between EBNA2 and CBFa/RBPJK," *Journal of Virology*, vol. 69, No. 3, pp. 1944–1950 (1995).

Yalamanchili et al., "Genetic and Biochemical Evidence that EBNA2 Interaction with a 63–kDa Cellular GTG–Binding Protein is Essential for B–lymphocyte Growth Transformation by EBV," *Virology*, vol. 204, No. 2, pp. 634–641 (1994).

*Primary Examiner*—Ali R. Salimi
*Attorney, Agent, or Firm*—Leydig, Voit & Mayer, Ltd.

[57] ABSTRACT

The present invention provides peptides having substantial homology with the CBF1/RBPJk interaction domain of EBNA2. The peptides preferably comprise between about ten and twenty amino acids. The peptides are able to compete with the native EBV EBNA2 protein for interaction with CBF1. The peptides thus can be employed as a pharmaceutical, e.g., along with an appropriate carrier in a pharmaceutical composition, particularly in a method of protecting against or treating EBV infection. The peptides also can be employed in a method of detecting factors that interact with the EBV EBNA2 protein.

7 Claims, 9 Drawing Sheets

```
A  ITT-----PLATSQTP--TTKQILPKTTRSSASMDPLPLPPLST PPPPAPSTPSPGIV  341
         **          *|*****    *|**** *|*****
B  HVPDQSMHPLTHQSTPNDP-DSPEPRSPTVFYNIPPMPLPPSQL PPPAAPAQPPPGII  309
   *       **  ******           **  **  * ***  *****   *|**|
C  HQLSLPPHPPPHQSTPHCSSDSTGLPPPPTSYSIPSMTLSPEPL PPPAAPAHPLPGVI  274
                                                    CR5

A  RDRPTSPRPL GPVWWPPV PLPEHKLAGPOLLTPSFDPPTPEEETVR KRVSRPRQ ATLRKPRPCRIPQR  409
       *      * ** ****  *                          *   *
B  NDQQLHHLPSGPPWWPPI CDPPQPSKTQGQSRGQSR--GRGRGRGRGRQ KGKSRDK QRKPGGPWRPE-   374
       **      ******  **    *                    *    * *      *    ***
C  YDQQALPPTPGPPWWPPV RDPTPTTQTPPTNTKQPGDQGQGRWRQ RGRSKGR GRMHKLPEPRRPG-    341
                 CR6                                    PKC

A  EHIPGT FSPRMPHLSPAVPL GPVHQPR-PNSSPSTSTPEGLPPQSVFPHVAPGPSTSQPL------  468
       *  * ** ***          **    ***
B  ---PNT SSPSMPELSPVLGL ---HQGQGAGDSPT------------PGPSNAAPVCRNSHTAT    419
       *  * ******         * *****                  ****   *|**
C  ---PCT SSPSMPQLSPVVSL ---HQGQGPENSPT------------PGPSTAGPVCRVTPSAT    386
               CR7

A  ----PL                                                     470 [SEQ ID NO:12]
     *|
B  PNVSPI                                                     425 [SEQ ID NO:13]
   * |***
C  PDISPI                                                     392 [SEQ ID NO:14]
```

FIG. 5

EBNA2 PEPTIDES AND METHODS OF USING SAME

CROSS REFERENCE TO RELATED APPLICATIONS

This application is a continuation of PCT US97/02243, which was filed on Feb. 12, 1997, designates the United States of America, was published as WO 97/30081 (the entirety of which is incorporated herein by specific reference thereto), and claims priority under 35 U.S.C. 119 (e) to U.S. provisional patent application Ser. No. 60/011,557, which was filed on Feb. 13, 1996.

STATEMENT AS TO RIGHTS TO INVENTIONS MADE UNDER FEDERALLY SPONSORED RESEARCH AND DEVELOPMENT

This invention was made with government support, Grant No. RO1 CA42245, awarded by the National Institutes of Health, and Grant Nos. FRA429 and VM155, awarded by the American Cancer Society. The government may have certain rights in this invention.

TECHNICAL FIELD OF THE INVENTION

The present invention relates to peptides having substantial homology with the CBF1/RBPJk interaction domain of EBNA2, and methods of using such peptides, e.g., to protect against or treat an Epstein-Barr viral infection and to detect factors interacting with the Epstein-Barr virus.

BACKGROUND OF THE INVENTION

Epstein-Barr virus (EBV) is associated with a variety of human cancers including Hodgkin's lymphoma, primary central nervous system lymphoma in AIDS, systemic lymphoma in AIDS, post-transplant lymphoproliferative disease (PTLD), nasal T cell lymphoma, undifferentiated gastric carcinoma, and nasopharyngeal carcinoma (Filipovich et al., In I. T. Magrath (ed.), *The Non-Hodgkin's Lymphomas*, (Williams and Wilkins, 135–154 (1990)); Herbst et al., *Proc. Natl. Acad. Sci.*, 88,4766–4770 (1991); MacMahon et al., *Lancet*, 338, 969–973 (1991); Miller, In B. N. Fields et al. (eds.), *Virology*, 2nd ed. (Raven Press, New York, 1921–1958, 1990); Staal et al.,*Am. J. Clin. Pathol.*, 91, 1–5 (1989)). There also has been a report of an association between EBV and human breast cancer. Primary infection in young adults results in infectious mononucleosis. Once infected, the individual carries the virus in B cells as a latent infection for life. Approximately 80–90% of the adult population in the United States is infected with this virus. In most cases the virus and host coexist uneventfully. However, the onset of immunosuppression, either clinically-induced in the case of transplant patients, or present as a consequence of other infections, for example in AIDS, leads to an increased risk for the development of EBV-associated malignant disease. There currently is no treatment available to eliminate the B cells latently infected with EBV that are the progenitors of these malignancies. Nucleoside analogs have some efficicacy in reducing lytic EBV infection but have no effect on the latently replicating virus since the EBV DNA polymerase and EBV thymidine kinase enzymes, which are the targets of the nucleoside analogs, are not expressed during latent infection. Accordingly, there remains a need for methods to prevent de novo EBV infection, and to treat latent EBV infection, particularly following organ transplantation, given that EBV plays such a substantial role in postransplantation morbidity and mortality (Kumar et al., *Am. J. Surg. Pathol.*, 17, 1046–1053 (1993); Randhawa et al., *Hepatology*, 21, 1751 (1995); Rosendale et al., *Arch. Pathol. Lab. Med.*, 119, 418–423 (1995)).

The EBV EBNA2 protein is one of the first viral proteins expressed after infection by EBV. EBNA2 is a transcriptional activator that regulates viral latency gene expression and activates expression of cellular genes (Abbott et al., *J. Virol.*, 64, 2126–2134 (1990); Calender et al., *Proc. Natl. Acad. Sci.*, 84, 8060–8064 (1987); Cohen et al.,*J. Virol.*, 65, 5880–5885 (1991); Cordier et al., *J. Virol.*, 64, 1002–1013 (1990); Ling et al., *Proc. Natl. Acad. Sci.*, 90, 9237–9241 (1993a); Rickinson et al., *J. Virol.*, 61, 1310–1317 (1987); Rooney et al., *J. Virol.*, 66, 496–504 (1992); Wang et al.,*J. Virol.*, 64, 2309–2318 (1990)). EBNA2 is critical for the establishment of a latent infection in the B cell and for initiating the changes in B cell growth that can ultimately lead to tumorigenesis. On primary infection of B cells, the latency W promoter (Wp) is used to express EBNA-LP and EBNA2 (Sample et al., *Proc. Natl. Acad. Sci.*, 83, 5096–5100 (1986); Speck et al., *Proc. Natl. Acad. Sci.*, 82, 8305–8309 (1985)). Expression of the EBNA genes then switches from the Wp to the latency C promoter (Cp), and this switch is controlled by EBNA2 (Bodescot et al., *J. Virol.*, 61, 3424–3430 (1987); Rooney et al., *J. Virol.*, 63, 1531–1539 (1989); Rooney et al. (1992), supra; Woisetschlager et al., *Proc. Natl. Acad. Sci.*, 87, 1725–1729 (1990); Woisetschlager et al., *Proc. Natl. Acad. Sci.*, 88, 3942–3946 (1991)). The promoters for the latency membrane proteins LMP-1 and LMP-2 (terminal protein) are also up-regulated by EBNA2 (Fahraeus et al., *Proc. Natl. Acad. Sci.*, 87, 7390–7394 (1990); Tsang et al., *J. Virol.*, 65, 6765–6771 (1991); Wang et al., *J. Virol.*, 65, 4101–4106 (1991); Zimber-Strobl et al., *J. Virol.*, 65, 415–423 (1991); Zimber-Strobl et al.,*EMBO J.*, 12, 167–175 (1993)), placing the entire program of latency gene expression under the influence of EBNA2. Further, the changes in surface expression of B cell activation antigens that are induced by EBV infection (Calender et al., *Proc. Natl. Acad. Sci.*, 84, 8060–8064 (1987); Rowe et al., *EMBO J.*, 6, 2743–2751 (1987)) are also recognized as being partially attributable to EBNA2. In particular, expression of CD21 and CD23 has been shown to be upregulated by EBNA2 (Cordier et al., supra; Rowe et al., supra; Wang et al., Proc. Natl. Acad. Sci., 84, 3452–3456 (1987); Wang et al. (1991), supra). Activation of cellular genes by EBNA2 thus appears to have an important role in altering B cell growth control.

The mechanism of EBNA2-mediated transactivation has become an area of intense investigation. EBNA2 does not bind directly to DNA, but rather targets promoters through interaction with a cellular DNA-binding protein designated CBF1 that binds to genes having upstream CBF1 binding sites (Ling et al.,*J. Virol.*, 68, 5375–5383 (1994); Ling et al., *J. Virol.*, 67, 2990–3003 (1993b); Zimber-Strobl et al. (1993), supra). Peptide sequencing and cloning recently revealed CBF1 to be identical to recombination binding protein J kappa (RBPJk) (Grossman et al., *Proc. Natl. Acad. Sci.*, 91, 7568–7572 (1994); Henkel et al., *Science*, 265, 92–95 (1994)). This latter protein was named on the basis of its ability to bind to the heptamer sequence in the immunoglobulin J kappa gene (Matsunami et al., *Nature*, 342, 934–937 (1989)). However, this binding ability was subsequently found to be artifactually generated by the addition of a BamHI linker to the heptamer probe (Grossman et al., supra; Henkel et al., supra). CBF1/RBPJk is highly conserved in sequence between species as divergent as humans and members of the genus Drosophila (Amakawa et al., Genomics, 17, 306–315 (1993); Furukawa et al., *J. Biol.*

Chem., 266, 23334–23340 (1991); Schweisguth et al., *Cell,* 69, 1199–1212 (1992)). In particular, the Drosophila homologue is encoded by the suppressor of hairless gene, and plays a key role in determination of neuronal cell fate (Furukawa et al., supra; Schweisguth et al., supra).

An examination of the binding site for CBF1/RBPJk reveals an essential core sequence, GTGGGAA that is necessary for binding, with flanking sequences influencing binding affinity (Ling et al. (1994), supra). The acceptable flanking sequences further have been defined by binding-site selection (Tun et al., *Nucleic Acids Res.,* 22, 965–971 (1994)), and a database search using this consensus sequence identifies CBF1/RBPJk-binding sites in a large number of cellular promoters. This confirms that EBNA2 has substantial potential to reprogram B cell gene expression. Along these lines, CBF1/RBPJk acts as a transcriptional repressor and may be a significant contributor to the downregulation of genes such as the surface activation antigens that are silent in quiescent B cells. By targeting CBF1/RBPJk, EBNA2 short-circuits this aspect of B cell regulatory control and can activate the CBF1/RBPJk repressed genes in the absence of the normal B cell proliferation signals.

In an effort to better understand the EBNA2 protein, the EBNA2 gene of the baboon lymphotropic virus, Herpesvirus papio (HVP), has been cloned and sequenced (Ling et al. (1993b), supra). A comparison of its amino acid sequence with that of the human type A (e.g., strain B95-8 or W91) and human type B (e.g., strain AG876) EBNA2 proteins (Dambaugh et al., *Proc. Natl. Acad. Sci.,* 81, 7632–7636 (1984)) reveals nine conserved regions, i.e., CR1 through CR9. CR8 5 contains the critical hydrophobic segment of the activation domain, and CR9 is a strong karyophilic signal sequence (Cohen et al. (1991), supra; Cohen et al., *J. Virol.,* 65, 2545–2554 (1991a); Ling et al. (1993b), supra). The conserved regions CR5, CR6, and CR7, which encompass the amino acids 252–425, contain the CBF1/RBPJk interaction domain in EBNA2.

A role for CR6 in CBF1/RBPJk binding previously had been suggested by the inability of a peptide carrying a double mutation of tryptophans 323 and 324 to interact with CBF1/RBPJk in an electrophoretic mobility shift assay (EMSA) (Ling et al. (1993a), supra; Ling et al. (1994), supra). However, these studies did not elucidate further critical regions of the protein necessary for CBF1 interaction. Similarly, through analysis of glutathione S-transferase (GST)-EBNA2 fusion proteins, EBNA2 amino acids 310–336 were identified as sufficient for CBF1/RBPJk interaction, and either the shorter sequence PPWWPP (i.e., Pro Pro Trp Trp Pro Pro [SEQ ID NO: 1]) or the longer sequence GPPWWPP (I/V) (C/R) DP (i.e., Gly Pro Pro Trp Trp Pro Pro (Ile/Val) (Cys/Arg) Asp Pro [SEQ ID NO: 2]) was suggested as possibly mediating this interaction (Tong et al., *J. Virol.,* 68, 6188–6197 (1994); Grossman et al., supra; Yalamanchili et al., *Virology,* 204, 634–641 (1994)). However, none of these studies went so far as to actually characterize the functional region for interaction, for instance, by determining whether a peptide comprising the region can compete with the native (i.e., wild-type) EBNA2 protein for CBF1 interaction. Furthermore, none of these studies has resulted in the synthesis of an EBNA2 peptide having sufficient biological activity (i.e., ability to compete with the native (i.e., wild-type) EBNA2 protein for CBF1 interaction) so as to comprise a potentially therapeutically effective clinical pharmaceutical agent.

Thus, precise definition of the CBF1/RBPJk interaction domain in EBNA2 would allow peptides comprising this region to be synthesized. This offers the possibility of manipulation of viral and/or cellular gene expression through application of the peptides. For instance, such peptides would find use in the study of B cell differentiation and modification thereof by EBV infection. Moreover, such peptides could be employed, for instance, in disrupting the interaction between CBF1 and EBNA2. This would allow the therapeutic use of the peptides, particularly as an anti-EBV agent (e.g., in preventing de novo EBV infection) and as an antitumor agent (e.g., in preventing EBNA2-initiated changes in B cell growth that can ultimately lead to tumorigenesis).

Accordingly, the present invention seeks to overcome at least some of the aforesaid limitations of the prior art. In particular, it is an object of the present invention to provide EBNA2 peptides comprising the CBF1/RBPJk interaction domain. These and other objects and advantages of the present invention, as well as additional inventive features, will be apparent from the description of the invention provided herein.

BRIEF SUMMARY OF THE INVENTION

The present invention provides peptides having substantial homology with the CBF1/RBPJk interaction domain of EBNA2 wherein the peptides comprise between about ten and about twenty amino acids. The peptides are able to compete with the native EBV EBNA2 protein for interaction with CBF1, and can be employed as a pharmaceutical, e.g., along with an appropriate carrier in a pharmaceutical composition, particularly in a method of protecting against or treating EBV infection. The peptides also can be employed in a method of detecting factors that interact with the EBV EBNA2 protein.

BRIEF DESCRIPTION OF THE FIGURES

FIG. 5 is a diagram that depicts alignment of the human type A (strain B95-8) (A), human type B (strain AG876) (B), and Herpesvirus papio (HVP) (C) EBNA2 amino acid sequences from residues 252 to 425. Clusters of amino acids that are conserved between all three EBNA2 proteins are indicated (boxes labeled "CR5", "CR6" and "CR7"), as is a positionally-conserved, putative PKC phosphorylation site (boxes labeled "PKC"). Asterisks denote amino acid identity, and vertical lines indicate amino acid similarity.

DETAILED DESCRIPTION OF THE INVENTION

Figure 1:
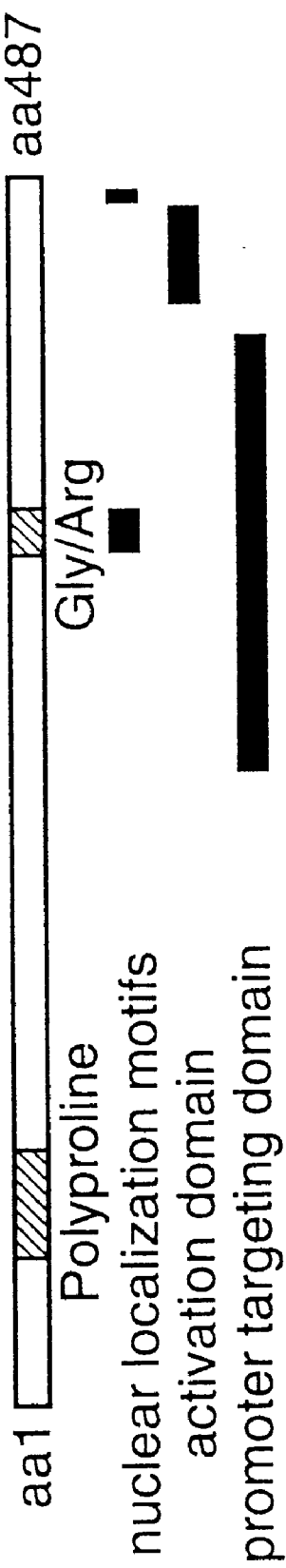
FIG. 1 is a diagram that depicts the relative positions of functional domains (i.e., nuclear localization motifs, activation domain, and promoter targeting or CBF1/RBPJk interaction domain) in the full length EBNA2 protein as black rectangles.

The present invention provides, among other things, biologically active peptides, i.e., peptides that are capable of competing with the native EBV EBNA2 protein for interaction with a cellular DNA-binding protein designated CBF1.

In this application, the conventional abbreviations for amino acids, peptides and their derivatives are used as generally accepted in the peptide art and as recommended by the IUPAC-IUB Commission on Biochemical Nomenclature (*European J. Biochem.*, 138, 9–37 (1984)). Similarly, peptide sequences are written according to the standard convention wherein the N-terminal amino acid is on the left and the C-terminal amino acid is on the right. The term "peptide" as used herein refers to any length molecular chain of amino acids linked by peptide bonds, so long as the length of the peptide is less than that of a full length (i.e., "wild-type" or "native") protein. The term "peptide" encompasses the term "polypeptide", which refers more specifically to a linear polymer of more than 10 amino acids.

The peptides of the present invention preferably are comprised of an amino end and a carboxyl end. The peptides can comprise D- or L-peptides, or a mixture of the D- and L-amino acid forms. However, the D-form of the amino acids are particularly preferred since peptides comprised of D-amino acids are expected to have a greater retention of their biological activity in vivo given that the D-amino acids are not recognized by naturally occurring proteases.

A peptide of the invention preferably is a peptide having substantial homology with the CBF1/RBPJk interaction domain of EBNA2 comprising the sequence Gln Leu His His Leu Pro Ser Gly Pro Pro Trp Trp Pro Pro Ile Cys Asp Pro Pro Gin [SEQ ID NO: 3], wherein the peptide comprises between about fifteen and about twenty amino acids. Desirably the peptide comprises the sequence of SEQ ID NO: 3. Optimally the peptide is deleted at either the N- or C-terminus, or both termini, by 1, 2, 3, 4, or 5 amino acids.

As referred to herein, a "peptide having substantial homology" is a variant peptide. A variant peptide is a peptide that is substantially homologous to another indicated peptide, but which has an amino acid sequence that differs from that peptide. The activity of the variant peptides can be confirmed using an EMSA as described in the Examples which follow, or using any assay by which the ability of the peptide to compete with native EBNA2 protein for CBF1 interaction can be confirmed. Qualitative results can be obtained by competitive autoradiographic plate binding assays, or Scatchard analysis can be employed to generate quantitative results.

The variant amino acid sequence preferably is at least 80% identical (where "identity" means the amino acids are the same) to an indicated peptide sequence, and, even more preferably, is at least 90% identical. The degree of homology (i.e., percent identity) can be determined, for instance, by comparing sequence information using a computer program optimized for such comparison (e.g., using the GAP computer program, version 6.0 or a higher version, described by Devereux et al. (*Nucleic Acids Res.*, 12, 387 (1984), and freely available from the University of Wisconsin Genetics Computer Group (UWGCG)).

In terms of the amino acids that are not identical between the variant and the reference peptide, the variant peptides preferably comprise conservative amino acid substitutions, i.e., such that a given amino acid is substituted by another amino acid of similar size, charge density, hydrophobicity/hydrophilicity, and/or configuration (e.g., Val for Phe).

In another preferred embodiment, preferably the peptide is a peptide having substantial homology with the CBF1/RBPJk interaction domain of EBNA2 comprising the sequence Gin Ser His Asn Leu Pro Ser Gly Pro Pro Trp Trp Pro Pro Ile Cys Asp Pro Pro Gin [SEQ ID NO: 4], wherein the peptide comprises between about fifteen and about twenty amino acids. Even more preferably, the peptide comprises the sequence of SEQ ID NO: 4, and optimally is deleted at either the N- or C-terminus, or both termini, by 1, 2, 3, 4, or 5 amino acids. Alternately, preferably the peptide is a peptide having substantial homology with the CBF1/RBPJk interaction domain of EBNA2 comprising the sequence Gin Ala Leu Pro Pro Thr Pro Gly Pro Pro Trp Trp Pro Pro Val Arg Asp Pro Thr Pro [SEQ ID NO: 5], wherein the peptide comprises between about fifteen and about twenty amino acids. Even more preferably, the peptide comprises the sequence of SEQ ID NO: 5, and optimally is deleted at either the N- or C-terminus, or both termini, by 1, 2, 3, 4, or 5 amino acids.

In yet another preferred embodiment, preferably the peptide is a peptide having substantial homology with the CBF1/RBPJk interaction domain of EBNA2 comprising the sequence Pro Ser Gly Pro Pro Trp Trp Pro Pro Ile [SEQ ID NO: 7], wherein the peptide comprises between about ten and about twenty amino acids. Optimally the peptide comprises the sequence of SEQ ID NO: 6. However, it also is preferable in some applications that any one of the first four amino acids of this sequence can be substituted, e.g., with any other amino acid.

Similarly, in still another preferred embodiment, preferably the peptide is a peptide having substantial homology with the CBF1/RBPJk interaction domain of EBNA2 comprising the sequence Thr Pro Gly Pro Pro Trp Trp Pro Pro Val [SEQ ID NO: 7], wherein the peptide comprises between about ten and about twenty amino acids. Desirably, the peptide comprises the sequence of SEQ ID NO: 7.

The peptides according to the invention can be prepared by any of a number of conventional techniques. For instance, in the case of recombinant peptides, a DNA fragment encoding a desired peptide can be subcloned into an appropriate vector using well known molecular genetic techniques (see, e.g., Maniatis et al., *Molecular Cloning: A Laboratory Manual,* 2nd ed. (Cold Spring Harbor Laboratory, 1989)). The fragment can be transcribed and the peptide subsequently translated in vitro. Commercially available kits can also be employed (e.g., such as manufactured by Clontech, Palo Alto, Calif.; Amersham Life Sciences, Inc., Arlington Heights, Ill.; InVitrogen, San Diego, Calif., and the like). The polymerase chain reaction optionally can be employed in manipulation of nucleic acids.

Alterations of the native amino acid sequence to produce variant peptides can be done by a variety of means known to those skilled in the art. For instance, site-specific mutations can be introduced by ligating into an expression vector a synthesized oligonucleotide comprising the modified site. Alternately, oligonucleotide-directed site-specific mutagenesis procedures can be used such as disclosed in Walder et al., *Gene,* 42, 133 (1986); Bauer et al., Gene, 37, 73 (1985); Craik, *Biotechniques,* 12–19 (January 1995); and U.S. Pat. Nos. 4,518,584 and 4,737,462.

Any appropriate expression vector (e.g., as described in Pouwels et al., *Cloning Vectors: A Laboratory Manual* (Elsevier, N.Y.: 1985)) and corresponding suitable host can be employed for production of recombinant peptides. Expression hosts include, but are not limited to, bacterial species within the genera Escherichia, Bacillus, Pseudomonas, Salmonella, mammalian or insect host cell systems including baculovirus systems (e.g., as described by Luckow et al., Bio/Technology, 6,47 (1988)), and established cell lines such as the COS-7, C127, 3T3, CHO, HeLa, BHK cell line, and the like. The ordinary skilled artisan is, of course, aware that the choice of expression host has ramifications for the type of peptide produced. For instance the glycosylation of peptides produced in yeast or mammalian cells (e.g., COS-7 cells) will differ from that of peptides produced in bacterial cells such as *Escherichia coli.*

Alternately, the peptides of the invention (including the variant peptides) can be synthesized using standard peptide synthesizing techniques well known to those of skill in the art (e.g., as summarized in Bodanszky, *Principles of Peptide Synthesis,* (Springer-Verlag, Heidelberg: 1984)). In particular, the peptides can be synthesized using the procedure of solid-phase synthesis (see, e.g., Merrifield, *J. Am. Chem. Soc.,* 85, 2149–54 (1963); Barany et al., *Int. J. Peptide Protein Res.,* 30, 705–739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the peptide from the resin can be accomplished by, for example, acid treatment at reduced temperature. The peptide-containing mixture can then be extracted, for instance, with dimethyl ether, to remove non-peptide organic compounds, and the synthesized peptides can be extracted from the resin powder (e.g., with about 25% w/v acetic acid). Following the synthesis of the peptide, further purification (e.g., using high performance liquid chromatography (HPLC)) optionally can be done in order to eliminate any incomplete peptides or free amino acids. Amino acid and/or HPLC analysis can be performed on the synthesized peptides to validate the identity of the peptide. For other applications according to the invention, it may be preferable to produce the peptides as part of a larger fusion protein, either by chemical conjugation, or through genetic means, such as are known to those skilled in the art.

If desired, the peptides of the invention (including the variant peptides) can be modified, for instance, by glycosylation, amidation, carboxylation, or phosphorylation, or by the creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus.

In particular, it is anticipated that the aforementioned peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising either a peptide or a variant peptide, wherein the molecule preferably further comprises a reporter group selected from the group consisting of a radiolabel, a fluorescent label, an enzyme, a substrate, a solid matrix, and a carrier.

Such molecules desirably are employed in a method according to the invention that detects a factor that interacts with Epstein-Barr virus EBNA2. This method preferably comprises the steps of: (a) preparing a sample comprising cells or components thereof (e.g., by suspending or homogenizing the cells), (b) contacting the sample with a molecule comprising a peptide according to the invention under conditions suitable to effect binding of the factor by the molecule (e.g. by contacting the sample with a molecule for a suitable time and under suitable temperature and pressure conditions such that interaction can occur); and (c) removing the bound factor from the sample. Preferably, unbound molecule comprising the peptide also is removed. Such removal can be carried out by a variety of means known to those skilled in the molecule art, for instance, by affixing the comprising the peptide to a solid support prior to contacting the sample, thus allowing sample separation. Desirably, binding is measured using an appropriate assay depending on the reporter group used (e.g., using a calorimetric or fluorometric reaction). Moreover, such a method also can be employed to monitor the ability of the molecule comprising the peptide to compete off a cellular factor such as CBF1 from binding to EBV EBNA2.

Moreover, the peptides (including the variant peptides) of the present invention also can be used in other ways which exploit the ability of the peptides to interfere with binding of the native EBNA2 protein to CBF1. For instance, the peptides can be employed to inhibit de novo EBV infection, to inhibit EBNA2-mediated cell changes that potentially result in cell malignancy, and as a research tool for studying the pathogenesis of EBV infection.

These aforementioned illustrative uses and recitation of benefits are by no means comprehensive, and it is intended that the present invention encompass such further uses which necessarily flow from, but are not explicitly recited, in the disclosure herein.

Accordingly, it is expressly contemplated by the invention that the peptides (including variant peptides) of the invention be administered to cells either in vitro or in vivo. This comprises a method of using the peptides as a pharmaceutical, which preferably comprises administering the peptide to a mammal, or to cells of a mammal and then returning the treated cells to the mammal. As used herein, "administering" comprises any means by which the peptides of the invention are applied to contact cells and compete with the interaction of native (i.e., wild-type) EBV EBNA2 for binding cellular factors such as CBF1. The method is not dependent on any particular means of administration and is not to be so construed. Means of administration are well known to those skilled in the art, and also are exemplified herein.

In particular, it is contemplated that the peptides of the invention preferably be employed in a method of protecting against, and optionally treating, Epstein-Barr virus infection, wherein the method comprises administering a peptide of the invention to a mammal (particularly a human), or to cells of a mammal (particularly a human), and then returning the treated cells to the mammal. Optimally the peptide is administered in an amount that is sufficient to inhibit interaction of Epstein-Barr virus EBNA2 with CBF1, as further described herein, and in the Examples that follow. Desirably the peptide is administered either prior to or following a transplant, and most preferably, the administration is continued until the patient's immune system is restored.

One skilled in the art will appreciate that suitable means of administration are available, and, although more than one route can be used for administration, a particular route can provide a more immediate and more effective reaction than another route. For instance, local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

Pharmaceutically acceptable excipients (e.g., carriers) also are well-known to those who are skilled in the art, and are readily available. The choice of excipient will be determined in part by the particular method used to administer the peptide. Accordingly, there is a wide variety of suitable formulations for use in the context of the present invention, and the invention expressly provide a pharmaceutical composition that comprises a peptide of the invention and a pharmaceutically acceptable carrier therefor. The following methods and excipients are merely exemplary and are in no way limiting.

Formulations suitable for oral administration can consist of (a) liquid solutions, such as an effective amount of the compound dissolved in diluent, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth. Pastilles can comprise the active ingredient in an inert base, such as gelatin and glycerin, or sucrose and acacia, emulsions, gels, and the like containing, in addition to the active ingredient, such excipients as are known in the art.

A peptide of the present invention (including a variant peptide), either alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, peptides of the present invention can be made into suppositories by mixing with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate. Further suitable formulations are found in Remington's Pharmaceutical Sciences, 17th ed., (Mack Publishing Company, Philadelphia, Pa.: 1985), and methods of drug delivery are reviewed in, for example, Langer, *Science,* 249, 1527–1533 (1990).

The dose administered to an animal, particularly a human, in the context of the present invention will vary with the peptide of interest, the composition employed, the method of administration, and the particular site and organism being treated. Generally, the "effective amount" of the composition is such as to produce the desired effect in a host. Generally this desired effect will be competition for interaction with cellular factors (e.g., CBF1) with which wild-type (i.e., native) EBV EBNA2 protein characteristically interacts. This can be monitored, for instance, using methods as described in the following Examples.

Generally, it is preferable that the peptides be administered in a dose of from about 1 to about 1,000 micrograms of the peptide per kg of the body weight of the host per day when given parenterally. However, this dosage range is merely preferred, and higher or lower doses may be chosen in appropriate circumstances. For instance, the actual dose and schedule can vary depending on whether the composition is administered in combination with other pharmaceutical compositions, or depending on interindividual differences in pharmacokinetics, drug disposition, and metabolism. One skilled in the art easily can make any necessary adjustments in accordance with the necessities of the particular situation.

If desired, the half-life of the peptides can be increased by conjugation to soluble macromolecules, such as polysaccharides, or synthetic polymers, such as polyethylene glycol, as described, for instance, in U.S. Pat. Nos. 5,116,964, 5,336,603, and 5,428,130. It may be desirable for certain applications that the conjugate vaccines (particularly the polymeric vaccines) are treated prior to use to eliminate nonimmunogenic conjugates (e.g., as described in U.S. Pat. Nos. 5,126,131 and 5,370,871). Alternately, the peptides can be "protected" in vesicles composed of substances such as proteins, lipids (for example, liposomes), carbohydrates, or synthetic polymers. If liposomes are employed, liposome delivery can be carried out as described in U.S. Pat. No. 5,468,481, or using liposomes having increased transfer capacity and/or reduced toxicity in vivo (see, e.g., PCT patent application WO 95/21259 and the references cited therein). Furthermore, peptides can be administered in conjunction with adenovirus (preferably replication-deficient adenovirus) to allow the intracellular uptake of the peptides by adenoviral-mediated uptake of bystander molecules (e.g., as described in PCT patent application WO 95/21259). Similarly, fusion of a peptide according to the invention to an antibody that recognizes a cell surface antigen can be employed to deliver the resultant fusion protein to a specific target cell or tissue (e.g., as described in U.S. Pat. No. 5,314,995).

The following examples further illustrate the present invention and, of course, should not be construed as in any way limiting its scope.

EXAMPLE 1

This example describes the contribution of hydrophobic residues in CR5, CR6 and CR7 to the stability of complex formation with CBF1/RBPJk.

The relative positions of the various functional domains the EBNA2 protein are depicted in FIG. 1. To define the amino acids required for interaction with CBF1, various synthetic peptides comprising the promoter targeting domain (i.e., the CBF1/RBPJk interaction domain) were constructed. The truncated and mutated peptides diagrammed in FIG. 2 were synthesized by in vitro transcription-translation, and were tested for their ability to form complexes with CBF1 that could be detected in an electrophoretic mobility shift assay (EMSA) (Ling et al., J. Virol., 69, 1944–1950 (1995)). The expressed peptides were tested using a fractionated extract of EBV negative lymphoblastoid CA46 cells (American Type Culture Collection, Rockville, Md.). The peptides were labeled with $^{35}$S-methionine, and their integrity was confirmed by sodium dodecylsulfate sulfate-polyacrylamide gel electrophoresis (SDS-PAGE). To ensure that equal amounts of the EBNA2 peptides were added to each binding reaction mixture, the SDS-PAGE bands were quantitated using a Molecular Dynamics Phosphorimager, and the volume of the samples was adjusted on the basis of peptide size and the number of methionine residues.

In particular, the peptides were constructed based on the DNA sequence of EBV type A B95-8 strain (Baer et al., Nature, 310, 207–211 (1985)). Although the EBNA2A gene is highly conserved, the laboratory lymphoblastoid cell line strain W91 is differentiated from B95-8 by 13 nucleotide substitutions and a codon insertion (Walling et al., J. Virol., 68, 7918–7926 (1994); Baer et al., Nature, 310, 207–211 (1984); Cohen et al., J. Virol., 65, 2545–2554 (1991)). In particular, strain W91 as compared to strain B95-8 comprises a thymidine-to-cytosine conversion at EBNA2 codon 314 that results in an amino acid change of Leu to Ser, and comprises a cytosine-to-adenine conversion at EBNA-2 codon 316 resulting in an amino acid change of His to Asn (Walling et al., supra).

Figure 2:
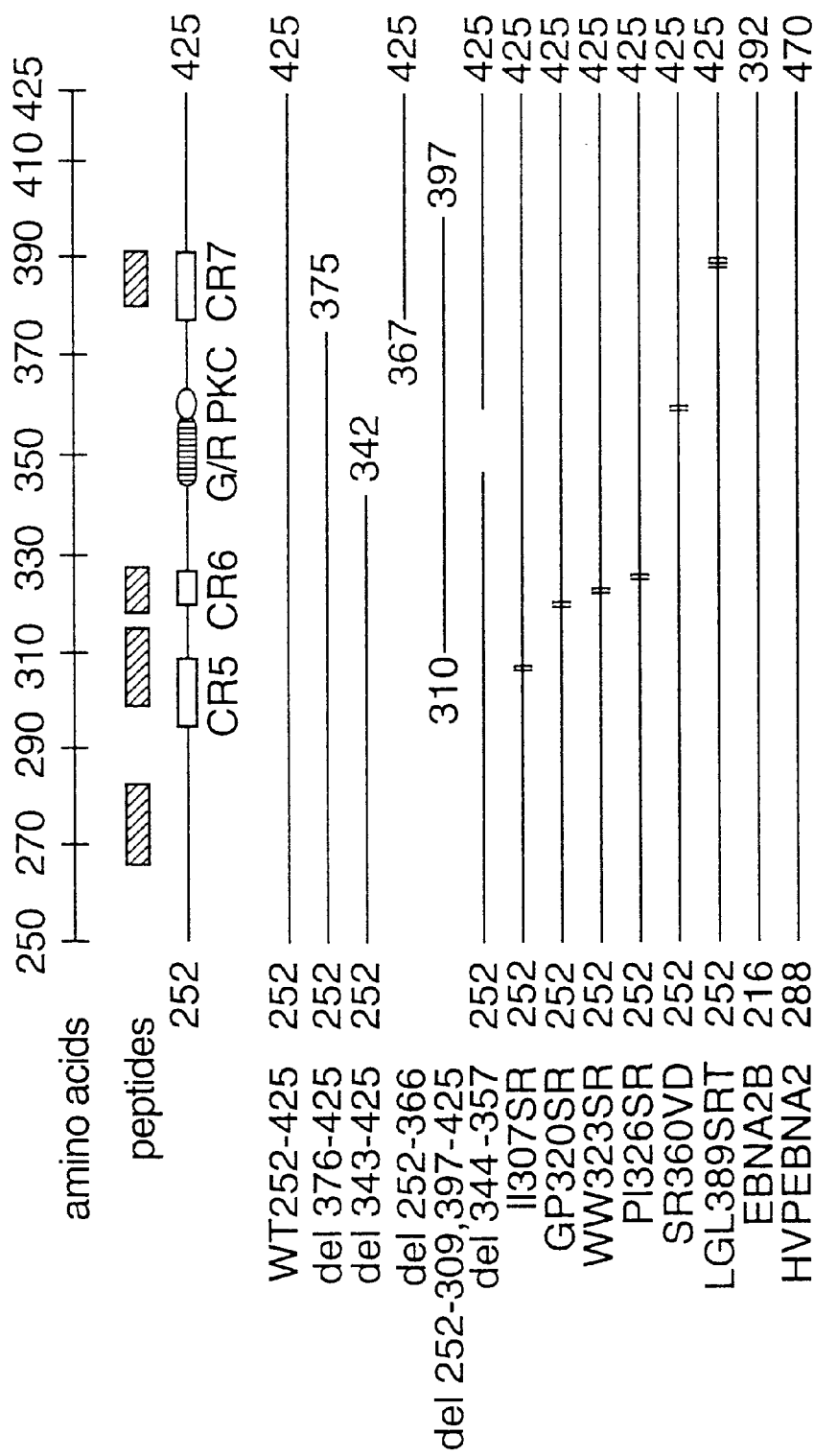
FIG. 2 is a diagram that depicts the CBF1/RBPJk interaction domain comprising amino acids 252–425, and summarizes mutations created in this domain. Shown are the regions synthesized as synthetic peptides (hatched bars), the locations of conserved motifs (open rectangles), a conserved, putative protein kinase C (PKC) phosphorylation site (oval), the glycine-arginine repeats (G/R) (hatched oval), the end points of deletions, and the positions of mutations introduced into this domain. In the peptides containing mutations, the wild-type amino acids are shown before the amino acid number, and the substituted amino acids are shown after the number (e.g., 11307SR).

As depicted in FIG. 2, a peptide lacking CR7 (i.e., del376-425 wherein amino acids 376 to 425 are deleted) inhibited the CBF1 complex by competition as effectively as a wild-type EBNA2 (i.e., E2) peptide comprised of amino acids 252–425. However, the E2/CBF1 complex formed of this interaction was reduced in amount and apparently was less stable than a complex formed with the larger peptide comprised of amino acids 252–425. Further truncation at the carboxy terminus resulted in a peptide, i.e., del343-425, that partially competed for the CBF1 complex but was unable to generate a stable E2/CBF1 complex. Peptides lacking CR5 and CR6 (i.e., del252-366) or lacking CR5 alone (i.e., del252-309,398-425) neither competed for the CBF1 complex nor formed a supershifted E2/CBF1 complex.

Figure 3:
FIG. 3 is an autoradiogram that depicts the effect of mutations on the ability of an EBNA2 (i.e., E2) peptide comprising amino acids 252–425 to interact with CBF1/RBPJk: probe (lane 1); E2 only (lane 2); lysate (lane 3); CBF1 (lane 4); CBF1 and lysate (lane 5); CBF1 and E2 252–425 (lane 6); CBF1 and del376–425 (lane 7); CBF1 and del343–425 (lane 8); CBF1 and del252–366 (lane 9); CBF1 and del252–309, del398–425 (lane 10); CBF1 and del344–357 (lane 11); CBF1 and II307SR (CR5) (lane 12); CBF1 and GP320SR (CR6) (lane 13); CBF1 and WW323SR (CR6) (lane 14); CBF1 and P1326SR (CR6) (lane 15); CBF1 and SR360VD (PKC) (lane 16); and CBF1 and LGL389SRT (CR7) (lane 17). Results of an EMSA using CBF1 purified by heparin-agarose chromatography and a 30-base pair oligonucleotide probe containing the Cp CBF1 binding site (Ling et al. (1993a), supra) are shown. The wild-type EBNA2 and mutant EBNA2 peptides spanning amino acids 252–425 were in vitro transcribed and translated, and equimolar amounts were added to the binding reactions. Addition of unprogrammed reticulocyte lysate to the CBF1 extract (+lysate) produced a minor bandshift that migrated in the range of the E2/CBF1 complex. The EBNA2/CBF1 complexes (i.e., E2/CBF1 complexes) vary in mobility depending on the size of the added EBNA2 peptide.

A concern with the use of truncated peptides is that the smaller peptide size might affect the ability to form stable complexes with CBF1 and influence the results obtained. Therefore, peptides comprised of amino acids 252–425 and carrying double and triple point mutations within CR5, CR6, and CR7, and within a conserved, putative protein kinase C (PKC) phosphorylation site, were generated as depicted in FIG. 2. Mutation of two hydrophobic residues in CR7 (i.e., LGL at position 389 changed to SRT, or LGL389SRT) produced a 50% reduction in the ability of amino acids 252–425 to form an EBNA2/CBF1 complex (FIG. 3). In contrast to this peptide, whose mutation resulted in a relatively small effect, peptides carrying mutations in hydrophobic residues in CR5 (i.e., II307SR) and CR6 (i.e., WW323SR and PI326SR) did not compete for the CBF1 complex and produced little or no EBNA2/CBF1 super-shifted complex. Mutation of two non-hydrophobic residues in CR6 (i.e., GP320SR) had no effect on the behavior of the peptide in the EMSA, which confirms that the hydrophobic residues in CR6 are functionally dominant. When considered in toto, the results suggest that CR7 makes a small contribution to the stability of the interaction with CBF1 but is not essential, whereas CR5 and CR6 are more important contributors to the stability of the EBNA2/CBF1 interaction.

The contribution of the glycine-arginine repeats (i.e., amino acids 346–356) and a putative PKC phosphorylation site (i.e., amino acids 357–363) also was examined.

Removal of the glycine-arginine repeats by deletion of amino acids 344–357 (i.e., del344-357) did not negatively affect EBNA2/CBF1 complex formation (FIG. 3), and mutation of the PKC site (i.e., SR360VD) had only a small effect, reducing EBNA2/CBF1 complex formation by 40% relative to the wild-type peptide.

EXAMPLE 2

This example describes the results of experiments that indicate that mutations in CR5 and CR6 also affect EBNA2 transactivation function.

Figure 4A:
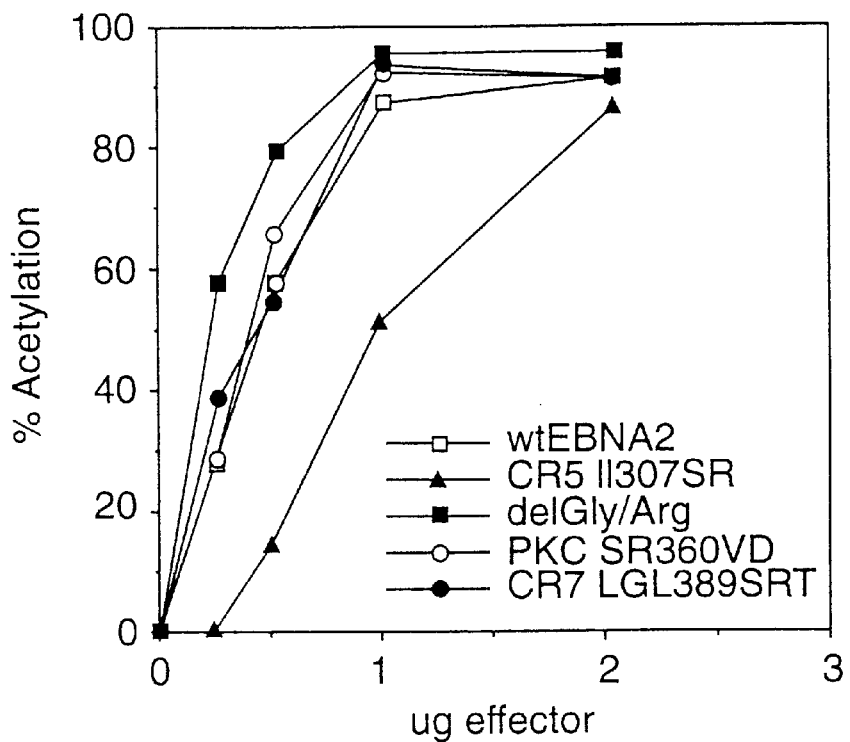
FIGS. 4A–4B are graphs that depict μg effector versus % acetylation for transactivation in DG75 cells of a Cp-CAT construction (Ling et al. (1993b), supra) cotransfected at 2 μg with increasing amounts (i.e., 0, 0.25, 0.5, 1.0 and 2.0 μg) of the indicated EBNA2 effector DNAs. Immunoblot analysis confirmed the equivalent expression of the different EBNA2 effector constructions in transfected cells.
Figure 4B:
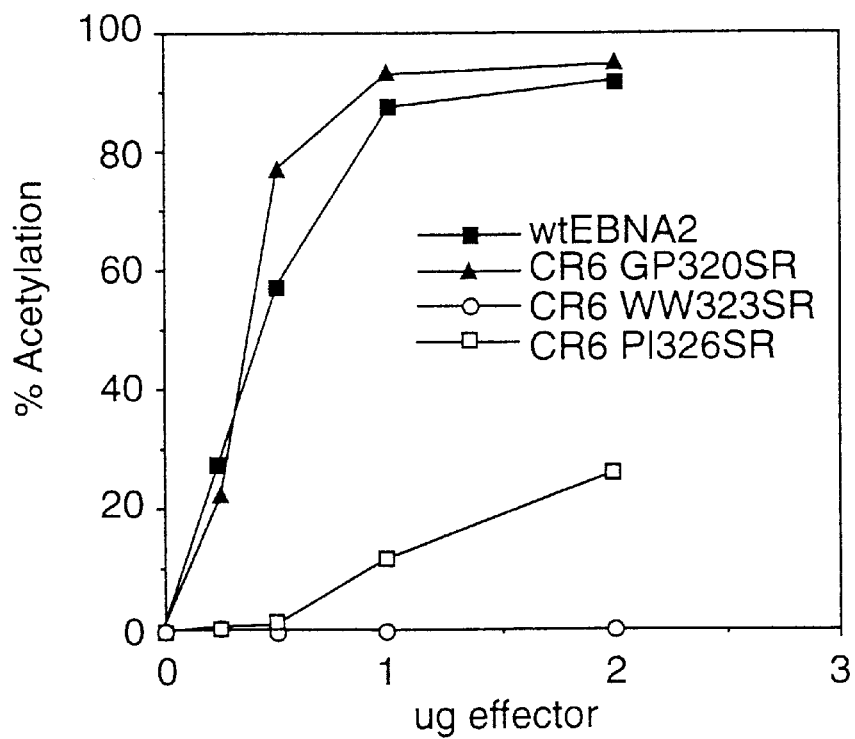

In order to correlate the effect of the mutations on CBF1 interaction measured in the in vitro binding assays with the effects on CBF1 interaction in vivo in cultured cells, the point mutations and the glycine-arginine deletion were incorporated into full-length EBNA2 proteins which were used to study EBNA2 targeting in transactivation assays. The mutant proteins were synthesized in equal abundance in transfected cells as assessed by Western blot analysis. FIGS. 4A and 4B compare the ability of wild-type and mutant EBNA2 proteins to transactivate expression from the EBV latency C promoter in a dose-response assay (Ling et al. (1993b), supra).

The CR7 and the PKC mutations exhibited a small (approximately two-fold) effect in reducing the amounts of EBNA2/CBF1 complex formed, and did not affect transactivation. The dose-response curves obtained with these mutants were indistinguishable from the wild-type EBNA2 response (FIG. 4A). It is possible that these mutations have some effect on protein conformation in the smaller 252–425 amino acid peptides used in the EMSA, and that this perturbation is compensated for in the context of the intact protein. The glycine-arginine deletion did not negatively affect complex formation in the EMSA, and the deleted EBNA2 protein transactivated the Cp-CAT target plasmid at 150% of wild-type levels in the linear range of the assay (i.e., 0.5 μg effector DNA).

The correlation between binding affinity as measured by EMSA and transactivation effectiveness was also observed with the CR5 and CR6 mutations. Mutation of the hydrophobic residues in CR5 impaired the ability of the 252–425 amino acid peptide to form an EBNA2/CBF1 complex. In this case, transactivation in the linear range of the assay was only 10% that of wild-type EBNA2 (FIG. 4A). Interestingly, the deficit could be overcome by increasing the amount of effector DNA. At the highest dose of EBNA2 (i.e., 2 μg), transactivation by the CR5 mutant approached wild-type levels. These results indicate that CR5 contributes to a local peptide conformation that stabilizes the EBNA2/CBF1 interaction or mediates stabilizing contacts with CBF1.

Mutation of non-hydrophobic residues in CR6 had no effect on complex formation in the EMSA. As expected, transactivation by such a mutant (i.e., CR6GP320SR) mirrored that of wild-type EBNA2 (FIG. 4B). The CR6 mutation WW323SR had previously been shown to abolish both complex formation with CBF1 and transactivation of the Cp (Ling et al. (1994), supra) (FIG. 3). The data in FIG. 4B confirm the inability of this mutant to transactivate the Cp even at high doses of effector. Mutation of the only other hydrophobic residue in CR6 (i.e., P1326SR) severely impaired the ability of the peptide to form a complex with CBF1 in an EMSA. Transactivation at 0.5 μg of effector was only 2% that of wild-type EBNA2 (FIG. 4B). In contrast to what was observed with the CR6 WW323SR mutant, transactivation was observed at the highest levels of effector DNA. However, even then, the response was only 20% that of wild-type.

Table 1 gives a quantitative summary of results of EMSAs and transient transfection experiments.

TABLE 1

Quantitative summary of results of EMSAs and transient transfection experiments

| Protein | % Complex formation[a] | % Transactivation[b] |
|---|---|---|
| aa252–425 (wild-type) | 100 | 100 |
| del1376–425 | 10 | NT |
| del1343–425 | <1 | NT |
| del252–366 | <1 | NT |
| del252–309,398–425 | <1 | NT |
| del344–357 | 100 | 150 |
| II307SR (CR5) | 20 | 20[c] |
| GP320SR (CR6) | 90 | 120 |
| WW323SR (CR6) | <1 | 0 |
| PI326SR (CR6) | 5 | 2[c] |
| SR360VD (PKC) | 60 | 110 |
| LGL389SRT (CR7) | 50 | 100 |

[a] Complex formation relative to that obtained with wild-type EBNA2 (252–425). The amount of EBNA2/CBF1 supershifted complex was quantitated by using a phosphoimager. The amount of nonspecific complex formation by the reticulocyte lysate alone was subtracted.
[b] Relative EBNA2 transactivation of the Cp determined from FIG. 3. Values were calculated at DNA concentrations that gave 50% acetylation for wild-type EBNA2.
NT, not tested.
[c] Mutant showed increased transactivation at higher concentrations of effector DNA.

These data are consistent with a model in which the hydrophobic residues in CR6 play a critical role in forming the contact interface between EBNA2 and CBF1, and the amino tryptophans 323 and 324 are essential for this interaction.

EXAMPLE 3

This example describes the results of experiments that indicate that the homologous domain of Herpesvirus papio (HVP) binds CBF1.

Figure 6:
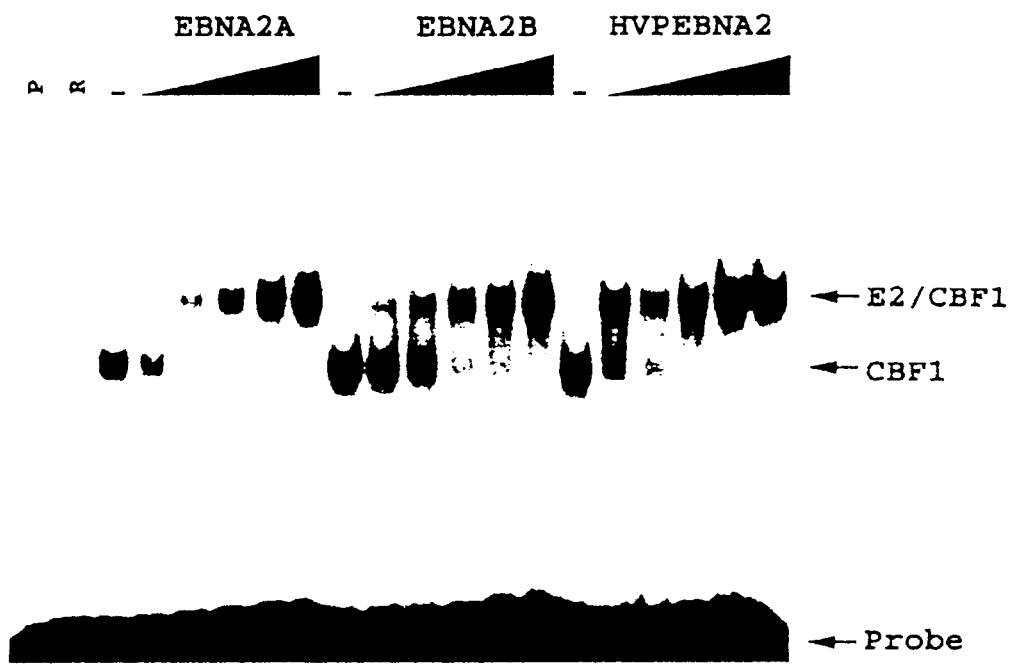
FIG. 6 is an EMSA that compares the ability of type A EBNA2 (i.e., EBNA2 comprising amino acids 252–425) and the homologous domains of type B (i.e., EBNA2 comprising amino acids 216–392) and HVP EBNA2 (i.e., HBP EBNA2 comprising amino acids 288–470) to form complexes with CBF1/RBPJk. The EBNA2 peptides and CBF1/RPBPJk were prepared by in vitro transcription and translation. EBNA2 peptides were added with two-fold increases in amount (black triangles) to a binding mixture containing a constant amount of CBF1/RBPJk and a 30-base pair Cp CBF1 binding site probe. Symbols: P, probe only; R, reticulolysate.

Outside of the three conserved regions CR5, CR6 and CR7, there is a low level of amino acid sequence conservation (23% identity) between human Type A, human Type B, and HVP EBNA2 proteins, as illustrated in FIG. 5. In particular, there are only 5 positionally conserved hydrophobic residues between amino acids 252 and 425. Two of these residues lie downstream of CR7 in a region that is unlikely to contribute to CBF1 interaction (i.e., based on the behavior of del376-425), and the other three occur immediately upstream of CR5. To validate that CR5 and CR6 contain the most important sequences for EBNA2/CBF1 complex formation, it is necessary to show that the same domain of HVP EBNA2 mediates interaction with CBF1. Accordingly, the homologous segment of HVP EBNA2 (i.e., amino acids 288–470) was translated in vitro, and the ability of this peptide to form a EBNA2/CBF1 complex was examined by EMSA (FIG. 6). The HVP peptide bound CBF1 as efficiently as did the type A EBNA2, converting all the DNA-bound CBF1 complex to the supershifted EBNA2/CBF1 complex. In view of the very low level of amino acid homology between HVP and the human isolates in the 252–425 amino acid targeting domain, these results confirm that CR5 and CR6 are the critical regions in effecting CBF1 interaction.

EXAMPLE 4

This example describes the results of experiments that indicate that type B EBNA2 binds CBF1 and transactivates gene expression in a manner comparable to type A EBNA2.

Type A EBV immortalizes B cells more efficiently than does type B virus, and this phenotype maps to EBNA2 (Cohen, *Proc. Natl. Acad. Sci.,* 89, 8030–8034 (1992)). It also has been reported that type A EBNA2 transactivates the cellular CD23 promoter more efficiently than does type B (Wang et al. (1991), supra). This raises the possibility that transactivation ability might contribute to the immortalization phenotype. Since the activation domains of the two proteins have been shown to have equivalent activity (Cohen et al., *Proc. Natl. Acad. Sci.,* 86, 9558–9562 (1989)), these experiments tested whether there is a difference in the ability of the type A and type B proteins to interact with CBF1. The type B EBNA2 gene was kindly provided by Dr. Elliott Kieff (Department of Microbiology and Molecular Genetics and Department of Medicine, Harvard Medical School).

Figure 7A:
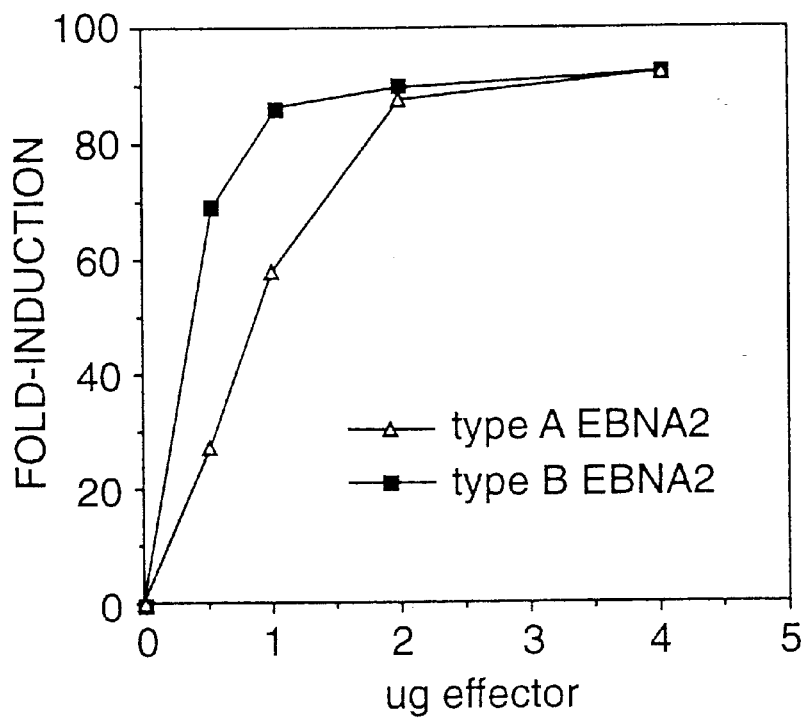
FIGS. 7A–7B are graphs that depict μg effector versus fold-induction for cotransfection assays comparing the ability of type A EBNA2 and type B EBNA2 to transactivate expression from Cp-CAT (FIG. 7A) and CD23p-CAT (FIG. 7B) (Ling et al. (1994), supra) in DG75 cells. The target plasmids were transfected at a constant amount (2 μg) and the effector DNAs at increasing amounts of 0, 0.25, 0.5, 1.0 and 2.0 μg.
Figure 7B:
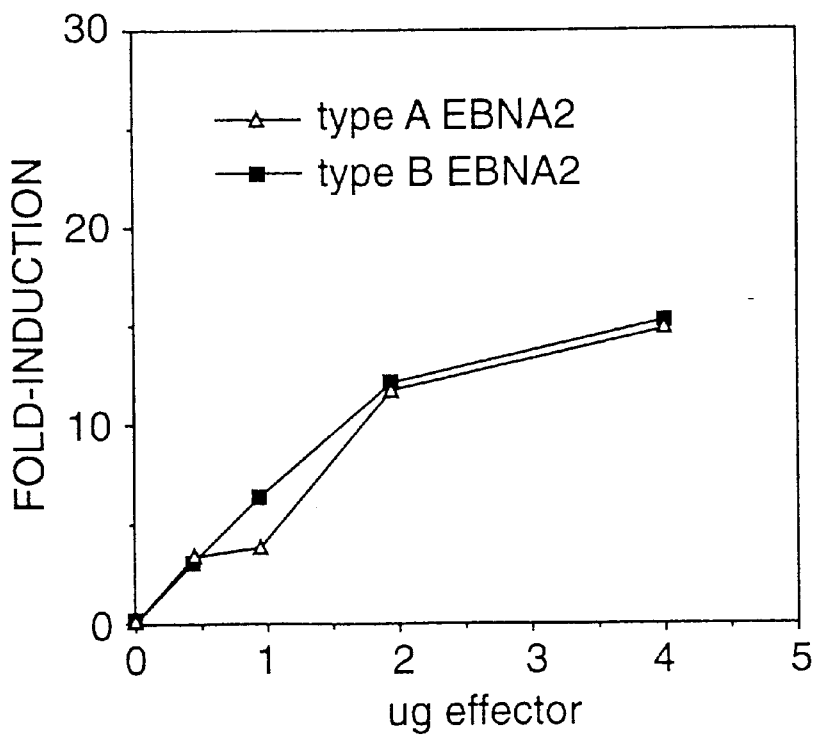

In an EMSA (FIG. 6), type B EBNA2 comprising amino acids 216–392 bound CBF1 comparably to type A EBNA2, although two-fold more of the type B peptide was required to achieve conversion of all the CBF1 to the supershifted complex. To evaluate whether this small difference in in vitro binding was biologically significant, transactivation efficiencies of the two proteins were examined in dose-response assays using the Cp and the CD23 promoters as targets. The type A and type B proteins are synthesized equally in transfected cells. Type B EBNA2 transactivated expression from a Cp reporter plasmid slightly better than did the type A protein at the lower doses of EBNA2, and equally at higher doses (FIG. 7A). The type B protein also has been reported to be more efficient at transactivating the LMP1 promoter (Wang et al. (1991), supra). Expression from the CD23 promoter construction was transactivated equally by the type A and type B proteins over a range of input effector DNA (FIG. 7B). Based on the observation that the type A and type B proteins interacted with CBF1 comparably, and that the type B protein was not at a disadvantage in transactivating either a viral or a cellular promoter in cotransfection assays, it is likely that other activities mediated by the amino-terminal half of type B EBNA2 are responsible for the inefficient immortalizing phenotype.

EXAMPLE 5

This example describes the results of experiments which indicate that a synthetic peptide comprised of amino acids 318–327 (i.e., CR6), can compete for EBNA2/CBF1 interaction, whereas a peptide mutated at tryptophans 323 and 324 cannot do so.

Overall, the EMSA and transactivation data implicate CR5 as contributing to the stability of the EBNA2/CBF1 interaction, and suggest that CR6, and, in particular, the tryptophan residues at 323 and 324, form a contact interface with CBF1. CR6 could perform this function by generating a specific secondary or tertiary structure that facilitates interaction (e.g., a lock and key model of interaction). Alternately, CR6 could mediate direct protein-protein contacts, perhaps through the formation of a tryptophan bridge (Corina et al., *Virology,* 197, 391–396 (1993)). To further examine the proposed contributions of CR5, CR6, and CR7 in EBNA2 interaction, and to probe the role of CR6, five 10–15 amino acid peptides were synthesized. The peptides were tested for their ability to compete with a full length EBNA2 protein for complex formation with CBF1. The relative location of the peptides in the EBNA2 protein is illustrated in FIG. 2, and the exact position of the sequences can be determined from FIG. 5. The peptides are as follows: a control peptide comprised of amino acids 265–279 (i.e., Ser Thr Pro Asn Asp Pro Asp Ser Pro Glu Pro Xaa Ser Pro Thr [SEQ ID NO: 8], wherein Xaa is Arg or Pro); a CR5 peptide comprised of amino acids 299–314 (i.e., Ala Pro Ala Gln Pro Pro Pro Gly Ile Ile Asn Asp Gln Gln Leu [SEQ ID NO: 9]); a CR6 peptide comprised of amino acids 318–327 (i.e., Pro Ser Gly Pro Pro Trp Trp Pro Pro Ile [SEQ ID NO: 6]); a CR6 WW323SR peptide comprised of amino acids 318–327 (i.e., Pro Ser Gly Pro Pro Ser Arg Pro Pro Ile [SEQ ID NO: 10]); and a CR7 peptide comprised of amino acids 380–391 (i.e., Pro Ser Met Pro Glu Leu Ser Pro Val Leu Gly Leu [SEQ ID NO: 11]).

Figure 8:
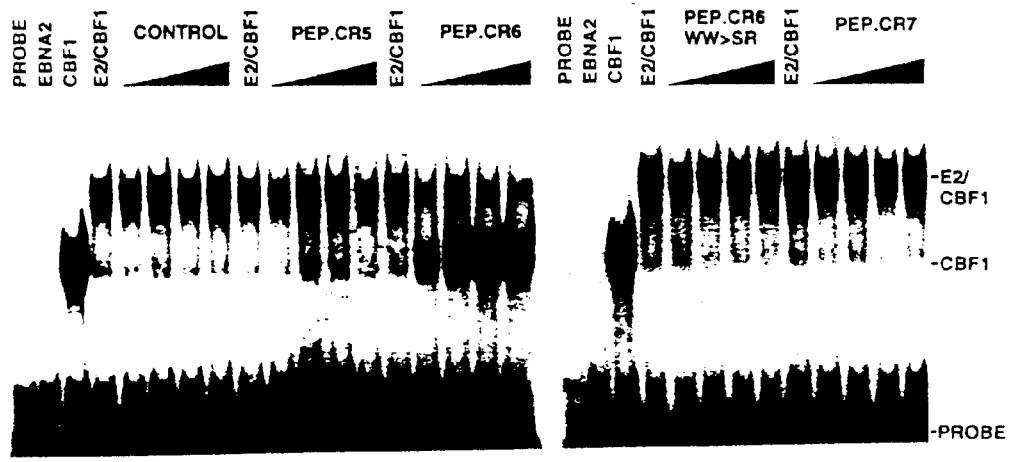
FIG. 8 is an EMSA that examines the ability of synthetic peptides representing CR5 (PEP.CR5), CR6 (PEP.CR6), mutant CR6 (CR6WW323SR) (PEP.CR6WW>SR), CR7 (PEP.CR7), and a control, nonconserved region comprising amino acids 265–279 (CONTROL) to compete for EBNA2/CBF1 complex formation. Increasing amounts of peptide (i.e., 1.25, 2.5, 5.0 and 10 μg; black triangles) were added to the binding reactions containing the Cp CBF1 binding site probe, in vitro translated wild-type EBNA2 (i.e., corresponding to amino acids 252–425) and heparin-agarose purified CBF1.

Increasing amounts of the peptides were added to the binding reaction mixtures which were then analyzed using an EMSA (FIG. 8). Neither the control peptide nor the peptides spanning CR5 or CR7 had any effect on the formation of the EBNA2/CBF1 complex. In contrast, addition of the 10 amino acid CR6 peptide eliminated by competition 40% of the EBNA2/CBF1 complex while at the same time regenerating the DNA-bound CBF1 complex to the levels seen in the absence of added EBNA2. It is known that EBNA2 can interact with CBF1 in solution (Grossman et al., supra; Henkel et al., supra). A typical binding reaction presumably contains both DNA-bound and non-DNA-bound EBNA2/CBF1 complexes. Glutathione S-transferase (GST) affinity assays using GST-EBNA2 (comprised of amino acids 252–425) and $^{35}$S-labeled, in vitro translated CBF1 confirmed that the CR6 peptide also could compete for EBNA2 interaction with CBF1 in solution. The amount of CBF1/EBNA2 complex detected by EMSA is therefore likely to be influenced by the equilibrium between DNA-bound and free CBF1/EBNA2 complexes, and by any difference in the affinity for DNA that CBF1 may exhibit when binding alone versus when binding as a CBF1/EBNA2 complex. Mutation of the tryptophan residues at positions 323 and 324 within an otherwise identical CR6 peptide abolished the ability of the peptide to compete with EBNA2 for interaction with CBF1 as assayed both by EMSA (FIG. 8) and in a GST affinity assay.

Thus, CR5 plays a role in generating an optimal local conformation for interaction with CBF1 and may make stabilizing protein-protein contacts. Critical protein-protein contacts are made by CR6. A 10 amino acid peptide is too small to establish a stable secondary structure. The fact that the 10 amino acid CR6 peptide was able to compete for EBNA2 binding to CBF1 and the inability of the peptide carrying the WW (i.e., Trp Trp) mutation to perform this function, indicates that the two tryptophan residues in CR6 are responsible for contacting CBF1. This interpretation conforms with the transactivation data which showed that only the WW mutation in CR6 could completely abolish transactivation function. The ability of such a small peptide to compete for EBNA2 binding to CBF1 confirms that targeting the disruption of this interaction appears to be a viable anti-viral strategy.

EXAMPLE 6

This example describes the results of experiments which indicate that the interaction of the viral EBNA2 peptide with a host cell protein (e.g., the CBF1 tethering protein) can be perturbed without perturbing the interaction of the host cell protein with other host cell factors.

The CBF1/RBPJk gene has been cloned and sequenced from human, mouse and Drosophila (Amakawa et al., supra; Furukawa et al., supra; Schweisguth et al., supra). The human protein comprises 500 amino acids, and the sequence is highly conserved in mouse and Drosophila. In Drosophila, the CBF1 homolog is encoded by the suppressor of hairless gene (Furukawa et al., supra; Schweisguth et al., supra). Loss of function alleles of suppressor of hairless (suH) cause lethality in the first day of pupal development. A "neurogenic" phenotype occurs in imaginal discs, and too many cells adopt a sensory organ precursor cell fate. Suppressor of hairless thus has a function in controlling peripheral nervous system development in Drosophila.

It recently was discovered that the suppressor of hairless gene functions by interacting with the Notch protein (Hsieh et al., Mol. Cell. Biol., 16, 952–959 (1996)). The Notch protein has been implicated in cell-cell signaling events that influence cell fate decisions. Similarly, the Notch protein has a human homolog (i.e., Tan-1) that has been implicated in T-lymphocyte malignancy (Ellisen et al., Cell, 66, 649–661 (1991)). These findings underscore the difficulty that can be encountered in efforts to perturb an interaction between a viral protein and a cellular tethering protein such as CBF1 as part of a larger effort to prevent viral infectivity and/or spread. Namely, with respect to the interaction of EBV EBNA2 and CBF1, the CBF1 tethering protein also interacts with other host cellular factors in modulating cell fate decisions. Perturbation of the so-called unnatural association of the viral protein and cellular tethering protein with use of a competing peptide could thus potentially also perturb the natural association of the cellular tethering protein with other host cell factors, and have an unwanted influence on B cell propagation and/or differentiation. This indicates that, at the very least, the contact points of the competing peptide and the host cell tethering protein need to be determined, and it must also be determined whether other cellular factors also contact the tethering protein in the same region as the competing peptide.

With respect to the present peptides, such further studies were carried out to avoid any deleterious effect on B cell growth or differentiation. It was determined that the CR6-based peptides interact with the same general region of CBF1 as do other cellular factors that play a role in cell—cell signaling. However, through manipulating the interactions of the cellular tethering protein, it was determined that the so-called natural and unnatural interactions could be uncoupled, and perturbed independently. In particular, a mutation can be introduced into the CBF1 protein which blocks the interaction of the CBF1 protein with other host cell factors, and which does not block the interaction of the CBF1 protein with the viral EBNA2 protein. These results thus further support that the peptides of the present invention can be employed, for instance, in therapy, without deleteriously influencing the interaction of the CBF1 tethering protein with other host cell factors.

EXAMPLE 7

This example describes the results of further experiments which confirm that the interaction of a viral EBNA2 peptide with a host cell protein (e.g., the CBF1 tethering protein) can be perturbed without perturbing the interaction of the host cell protein with other host cell factors.

CBF1, the cellular protein that targets EBNA2 to the regulatory sequences of both viral and cellular genes, also plays a central role in Notch signal transduction in the uninfected cell. It was demonstrated that a 10 amino acid peptide can compete for EBNA2 interaction with CBF1 (see, e.g., Example 5). Blocking this interaction would abolish EBNA2 function and provides a potential anti-EBV drug strategy. However, both EBNA2 and Notch interact with the repression domain of CBF1. An effective intervention strategy is dependent on the ability to interfere with EBNA2 binding without disrupting normal cellular Notch-CBF1 interactions. If Notch and EBNA2 recognized the same interaction interface on CBF1, then such a strategy would not be viable. However, a CBF1 mutant, KLV249AAA, was obtained which prevents CBF1 interaction with both the Notch1 and Notch2 proteins expressed in uninfected B cells but does not affect CBF1 interaction with EBNA2. The behavior of this mutant confirms that the Notch and EBNA2 interfaces can be discriminated and that selective abolition of EBNA2 binding can be achieved. Portions of these studies also are reported in Hsieh et al., "Epstein-Barr Virus Immortalization: Notch2 Interacts with CBF1 and Blocks Differentiation," J. Virol, 71(3) in press (March 1997).

In particular, a series of amino acid substitutions across the repression domain were generated in an intact CBF1 background and expressed as GAL4-CBF1 fusions. A variety of constructs were employed in generating the fusions. For instance, a eukaryotic expression vector, HA-E2TANLS, containing the hemagglutinin (HA) epitope at the 5' translation start site and the cDNA which encodes the EBNA2 transactivation domain and nuclear localization signal (E2TANLS) in the SG5 background has been described previously (Hsieh et al., Mol. Cell. Biol., 16,952–959 (1996)). PCR fragments representing different segments of either mouse Notch1 (N1) or rat Notch2 (N2) were introduced in frame into a BglII cloning site between HA and E2TANLS to generate individual N1-E2TANLS orN2-E2TANLS constructions. PCR fragments of Notch2 were cloned into the BglII site 3' of the GAL4 DNA binding domain in pGH250 to generate GAL4-Notch2IC fusions, and in pJH253 to generate SG5-FLAG-Notch2 fusions. The CBF1 mutant GAL4CBF1 (EEF233AAA), which lacks repression function, also was employed. The different GAL4-CBF1s, 5xGAL4TKCAT, and TKLuc have been described (Hsieh et al. (1996), supra). All the constructs were sequenced. Most of the Notch constructions were shown to express comparable amounts of the correctly sized proteins by immunoblot analysis using appropriate anti-HA (Babco), anti-GAL4 (Upstate Biotechnology) or anti-Flag (Eastman Kodak Co., New Haven, Conn.) antibody. The cDNA for rat Notch2 (aa1 789–2472) was cloned into the XbaI site of the pBOS vector to generate pBOS-CDN2.

The ability of the fusion proteins to interact with Notch1 and Notch2 was investigated. Mammals express at least four homologs, Notch1, Notch2, Notch3 and Notch4. Rodent Notch2 is expressed at 50-fold-higher levels than Notch1 in adult rat spleen (Weinmaster et al., Development, 116, 931–941 (1992)), which suggests that Notch2 may be more biologically relevant to models of EBV immortalization than Notch1. The Notch1 and Notch2 proteins employed were deleted Notch receptors (such deleted receptors are reviewed in Greenwald, Curr. Opin. Gen. Devel., 4, 556–562 (1994)), composed only of the intracellular domain (i.e., NotchIC). Such a truncated Notch receptor translocates to the nucleus, and functions as a ligand-activated receptor (Hsieh et al. (March 1997; in press), supra).

For these studies, HeLa cells were maintained in DMEM plus 10% fetal calf serum, and plated the day before transfection. Cotransfected HeLa cells received 6 μg of 5xGAL4TKCAT, 1 μg of wild-type or indicated GAL4-CBF1, 1 μg of the Notch1IC, Notch2IC, or NotchIC-E2TANLS (EBNA2) expression plasmid, and 1 μg of TKLuc as an internal control for transfection efficiency. Transient transfection, CAT assays, and luciferase assays were performed as previously described (Hsieh et al. (1996), supra). All assays were repeated three times.

One of the twelve CBF1 mutants tested, i.e., GAL4-CBF1 (KLV249AAA), lost its ability to interact with both Notch1IC and Notch2IC, and yet retained the ability to interact with EBNA2 (Table 2).

TABLE 2

Comparison of the ability of CBF1 fusion proteins to interact with Notch and EBNA2.
Relative CAT Activity*

| CAT | Reporter Alone | Notch1IC | Notch2IC | EBNA2 |
|---|---|---|---|---|
| Wild-type | 0.2 | 4.9 | 5.7 | |
| EEF233AAA | 1.4 | 4.2 | 4.5 | |
| KLV249AAA | 1.3 | 1.3 | 1.3 | 21 |

*Relative CAT activity was calculated by comparison with the transfected CAT reporter alone. This behavior of the KLV249AAA mutant indicates that the loss of interaction was not due to gross protein misfolding and, further, that the Notch and EBNA interactions can be physically distinguished.

Figure 9:
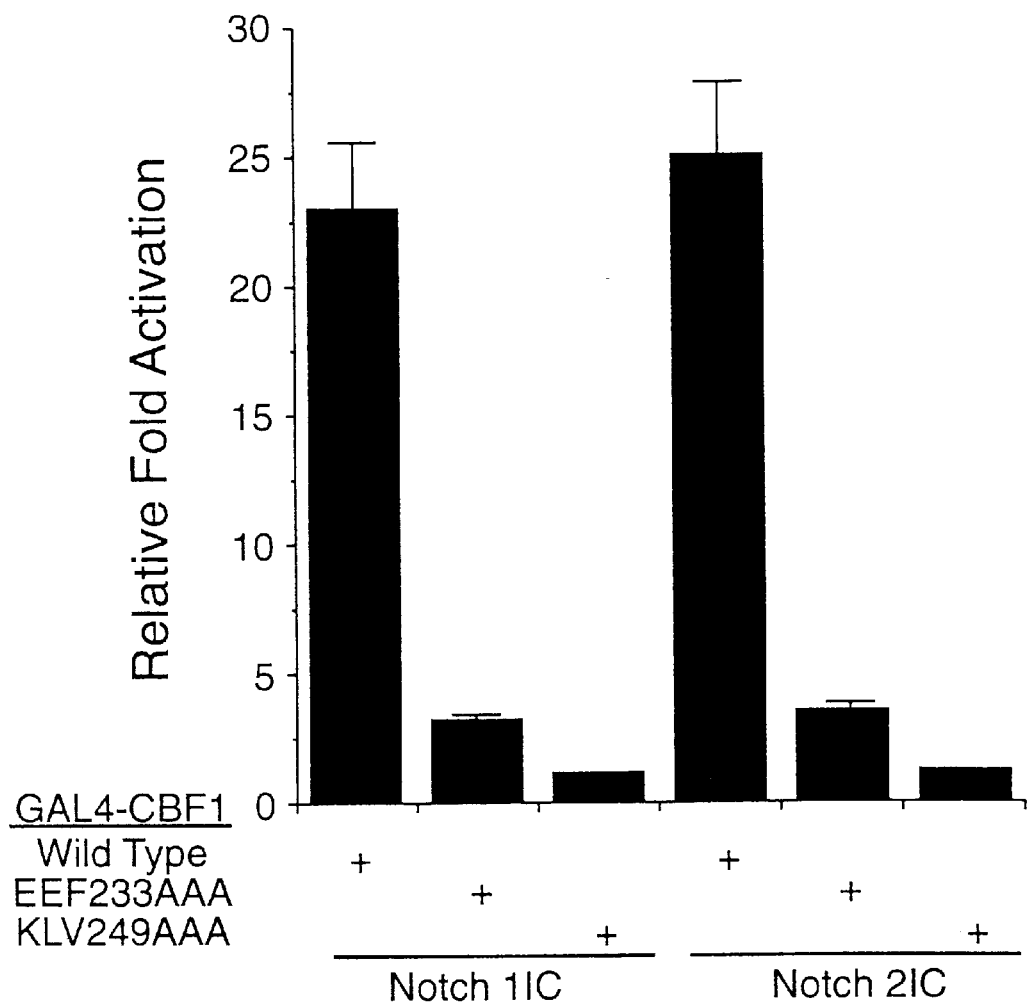
FIG. 9 is a graph that depicts fold-activation relative to the activity seen in the absence of Notch 1IC or Notch 21C for individual GAL4-CBF1 constructions (as further described in Table 2). The average and standard deviation for three independent experiments are provided.

The data from Table 2 was recalculated in terms of 'fold-activation' relative to the activity seen in the absence of Notch1IC or Notch2IC for the individual GAL4-CBF1 constructions (FIG. 9). As can be seen in FIG. 9, in each case, the fold-activation was greater in the presence of the wild-type CBF1 than the loss of repression mutant CBF1 (EEF233AAA). This indicates that Notch2IC, like Notch1IC and EBNA2, masks the repression domain of CBF1. The GAL4-CBF1 mutant (KLV249AAA) failed to mediate either Notch1IC or Notch2IC transactivation of CAT gene expression, indicating that both Notches target the same critical amino acids of CBF1. This mutant (KLV249AAA) retains EBNA2 interaction.

Thus, collectively these results indicate that the same three amino acids of CBF1 (249–251) are critical for both Notch1IC and Notch2IC interaction. None of the twelve mutations engineered into CBF1 blocked EBNA2 interaction and, hence, the precise location of the EBNA2 contact point within the repression domain remains to be determined. The ability of the KLV249AAA mutation to prevent CBF1 interaction with both Notch proteins but not EBNA2 also has implications for antiviral therapeutic strategies. It has been demonstrated that a 10 amino acid peptide representing EBNA2 sequences across conserved region 6 (CR6) can compete for EBNA2 interaction with CBF1 (see, e.g., Example 5). Blocking this interaction would abolish EBNA2 function and provides a potential anti-EBV drug strategy. However, such a strategy is dependent on the ability to interfere with EBNA2 without disrupting normal cellular Notch-CBF1 interactions. If Notch and EBNA2 recognized an identical interaction interface on CBF1, then such a strategy would not be viable. The behavior of the KLV249AAA variant confirms that the Notch and EBNA2 interfaces can be discriminated and that selective abolition of EBNA2 binding is feasible. The KLV249AAA mutation, like the previously described EEF233AAA mutation, also abolished CBF1 repression function. The core repression domain therefore encompasses amino acids between 233 and 249. CBF1 may mediate repression either by directly contacting the basal transcriptional machinery or through indirect contacts mediated by a co-repressor. The latter mechanism is favored since a CBF1 interacting protein with repressor function has been identified in a yeast two-hybrid screen.

All of the references cited herein, including the published literature, patents, and PCT applications, are hereby incorporated in their entireties by reference.

While this invention has been described with emphasis upon preferred embodiments, it will be obvious to those of ordinary skill in the art that the preferred embodiments can be varied. It is intended that the invention can be practiced otherwise than as specifically described herein. Accordingly, this invention includes all modifications encompassed within the spirit and scope of the appended claims.

What is claimed is:

1. A variant of the peptide

Pro Ser Gly Pro Pro Trp Trp Pro Pro Ile (SEQ ID NO: 6), wherein said variant comprises from about ten to about twenty amino acids, said variant is at least 80% or more identical to SEQ ID NO: 6, and said variant competes with native EBNA2 protein for CBF1.

2. The variant of claim 1, wherein said variant comprises SEQ ID NO: 6 in which any one of the first four amino acids is substituted with any other amino acid.

3. The variant of claim 1, wherein said variant is at least 90% or more identical to SEQ ID NO: 6.

4. A molecule comprising a variant of claim 1 and a reporter group selected from the group consisting of a radiolabel, a fluorescent label, an enzyme a substrate. a solid matrix and a carrier.

5. A pharmaceutical composition comprising (i) a variant of claim 1 or a peptide comprising from about ten to about twenty amino acids, wherein said peptide comprises SEQ ID NO: 6 and competes with native EBNA2 protein for CBF1, and (ii) a pharmaceutically acceptable carrier.

6. A method of using a variant of claim 1 or a peptide comprising from about ten to about twenty amino acids, wherein said peptide comprises SEQ ID NO: 6 and competes with native EBNA2 protein for CBF1, as a pharmaceutical agent, wherein said method comprises administering said variant or said peptide to a mammal, or to isolated cells of a mammal and then returning the isolated cells to which have been administered said variant or said peptide to said mammal.

7. A method of inhibiting Epstein-Barr virus (EBV) infection of a mammal, which method comprises administering a variant of claim 1 or a peptide comprising from about ten to about twenty amino acids, wherein said peptide comprises SEQ ID NO: 6 and competes with native EBNA2 protein for CBF1, to a mammal, or to isolated cells of a mammal and then returning the isolated cells to which have been administered said variant or said peptide to said mammal, with the proviso that said variant or said peptide is administered in an amount sufficient to inhibit interaction of EBV EBNA2 protein with CBF1.

* * * * *

SEQUENCE LISTING

<160> NUMBER OF SEQ ID NOS: 14

<210> SEQ ID NO 1
<211> LENGTH: 6
<212> TYPE: PRT
<213> ORGANISM: Epstein-Barr Virus

<400> SEQUENCE: 1

Pro Pro Trp Trp Pro Pro
 1               5

<210> SEQ ID NO 2
<211> LENGTH: 11
<212> TYPE: PRT
<213> ORGANISM: Epstein-Barr Virus
<220> FEATURE:
<221> NAME/KEY: SITE
<222> LOCATION: (8)
<223> OTHER INFORMATION: Xaa can be either Ile or Val
<220> FEATURE:
<221> NAME/KEY: SITE
<222> LOCATION: (9)
<223> OTHER INFORMATION: Xaa can be either Cys or Arg

<400> SEQUENCE: 2

Gly Pro Pro Trp Trp Pro Pro Xaa Xaa Asp Pro

```
                    1               5                  10

<210> SEQ ID NO 3
<211> LENGTH: 20
<212> TYPE: PRT
<213> ORGANISM: Unknown
<220> FEATURE:
<223> OTHER INFORMATION: Description of Unknown Virus Organism:
      Artificial

<400> SEQUENCE: 3

Gln Leu His His Leu Pro Ser Gly Pro Pro Trp Trp Pro Pro Ile Cys
  1               5                  10                  15

Asp Pro Pro Gln
            20

<210> SEQ ID NO 4
<211> LENGTH: 20
<212> TYPE: PRT
<213> ORGANISM: Unknown
<220> FEATURE:
<223> OTHER INFORMATION: Description of Unknown Virus Organism:
      Artificial

<400> SEQUENCE: 4

Gln Ser His Asn Leu Pro Ser Gly Pro Pro Trp Trp Pro Pro Ile Cys
  1               5                  10                  15

Asp Pro Pro Gln
            20

<210> SEQ ID NO 5
<211> LENGTH: 20
<212> TYPE: PRT
<213> ORGANISM: Unknown
<220> FEATURE:
<223> OTHER INFORMATION: Description of Unknown Virus Organism:
      Artificial

<400> SEQUENCE: 5

Gln Ala Leu Pro Pro Thr Pro Gly Pro Pro Trp Trp Pro Pro Val Arg
  1               5                  10                  15

Asp Pro Thr Pro
            20

<210> SEQ ID NO 6
<211> LENGTH: 10
<212> TYPE: PRT
<213> ORGANISM: Unknown
<220> FEATURE:
<223> OTHER INFORMATION: Description of Unknown Virus Organism:
      Artificial

<400> SEQUENCE: 6

Pro Ser Gly Pro Pro Trp Trp Pro Pro Ile
  1               5                  10

<210> SEQ ID NO 7
<211> LENGTH: 10
<212> TYPE: PRT
<213> ORGANISM: Unknown
<220> FEATURE:
<223> OTHER INFORMATION: Description of Unknown Virus Organism:
      Artificial

<400> SEQUENCE: 7

Thr Pro Gly Pro Pro Trp Trp Pro Pro Val
```

-continued

<210> SEQ ID NO 8
<211> LENGTH: 15
<212> TYPE: PRT
<213> ORGANISM: Unknown
<220> FEATURE:
<221> NAME/KEY: SITE
<222> LOCATION: (12)
<223> OTHER INFORMATION: Xaa can be either Arg or Pro
<220> FEATURE:
<223> OTHER INFORMATION: Description of Unknown Virus Organism:
      Artificial

<400> SEQUENCE: 8

Ser Thr Pro Asn Asp Pro Asp Ser Pro Glu Pro Xaa Ser Pro Thr
 1               5                  10                  15

<210> SEQ ID NO 9
<211> LENGTH: 15
<212> TYPE: PRT
<213> ORGANISM: Epstein-Barr Virus

<400> SEQUENCE: 9

Ala Pro Ala Gln Pro Pro Pro Gly Ile Ile Asn Asp Gln Gln Leu
 1               5                  10                  15

<210> SEQ ID NO 10
<211> LENGTH: 10
<212> TYPE: PRT
<213> ORGANISM: Epstein-Barr Virus

<400> SEQUENCE: 10

Pro Ser Gly Pro Pro Ser Arg Pro Pro Ile
 1               5                  10

<210> SEQ ID NO 11
<211> LENGTH: 12
<212> TYPE: PRT
<213> ORGANISM: Epstein-Barr Virus

<400> SEQUENCE: 11

Pro Ser Met Pro Glu Leu Ser Pro Val Leu Gly Leu
 1               5                  10

<210> SEQ ID NO 12
<211> LENGTH: 180
<212> TYPE: PRT
<213> ORGANISM: Unknown
<220> FEATURE:
<223> OTHER INFORMATION: Description of Unknown Virus Organism:
      Artificial

<400> SEQUENCE: 12

Ile Thr Thr Pro Leu Ala Thr Ser Gln Thr Pro Thr Lys Gln Ile
 1               5                  10                  15

Leu Pro Lys Thr Thr Arg Ser Ser Ala Ser Met Asp Pro Leu Pro Leu
                20                  25                  30

Pro Pro Leu Ser Thr Pro Pro Pro Ala Pro Ser Thr Pro Ser Pro
            35                  40                  45

Gly Ile Val Arg Asp Arg Pro Thr Ser Pro Arg Pro Leu Gly Pro Val
        50                  55                  60

Trp Trp Pro Pro Val Pro Leu Pro Glu His Lys Leu Ala Gly Pro Asp
 65                 70                  75                  80

```
Leu Leu Thr Pro Ser Phe Asp Pro Pro Thr Pro Glu Glu Thr Val
                85                  90                  95

Arg Lys Arg Val Ser Arg Pro Arg Gln Ala Thr Leu Arg Lys Pro Arg
            100                 105                 110

Pro Cys Arg Ile Pro Gln Arg Glu His Ile Pro Gly Thr Phe Ser Pro
            115                 120                 125

Arg Met Pro His Leu Ser Pro Ala Val Pro Leu Gly Pro Val His Gln
        130                 135                 140

Pro Arg Pro Asn Ser Ser Pro Ser Thr Ser Thr Pro Glu Gly Leu Pro
145                 150                 155                 160

Pro Gln Ser Val Phe Pro His Val Ala Pro Gly Pro Ser Thr Ser Gln
                165                 170                 175

Pro Leu Pro Leu
            180

<210> SEQ ID NO 13
<211> LENGTH: 173
<212> TYPE: PRT
<213> ORGANISM: Unknown
<220> FEATURE:
<223> OTHER INFORMATION: Description of Unknown Virus Organism:
      Artificial

<400> SEQUENCE: 13

His Val Pro Asp Gln Ser Met His Pro Leu Thr His Gln Ser Thr Pro
  1               5                  10                  15

Asn Asp Pro Asp Ser Pro Glu Pro Arg Ser Pro Thr Val Phe Tyr Asn
                20                  25                  30

Ile Pro Pro Met Pro Leu Pro Ser Gln Leu Pro Pro Pro Ala Ala
            35                  40                  45

Pro Ala Gln Pro Pro Pro Gly Ile Ile Asn Asp Gln Gln Leu His His
        50                  55                  60

Leu Pro Ser Gly Pro Pro Trp Trp Pro Pro Ile Cys Asp Pro Pro Gln
 65                 70                  75                  80

Pro Ser Lys Thr Gln Gly Gln Ser Arg Gly Gln Ser Arg Gly Arg Gly
                85                  90                  95

Arg Gly Arg Gly Arg Gly Arg Gly Lys Gly Lys Ser Arg Asp Lys Gln
            100                 105                 110

Arg Lys Pro Gly Gly Pro Trp Arg Pro Glu Pro Asn Thr Ser Ser Pro
        115                 120                 125

Ser Met Pro Glu Leu Ser Pro Val Leu Gly Leu His Gln Gly Gln Gly
        130                 135                 140

Ala Gly Asp Ser Pro Thr Pro Gly Pro Ser Asn Ala Ala Pro Val Cys
145                 150                 155                 160

Arg Asn Ser His Thr Ala Thr Pro Asn Val Ser Pro Ile
                165                 170

<210> SEQ ID NO 14
<211> LENGTH: 176
<212> TYPE: PRT
<213> ORGANISM: Unknown
<220> FEATURE:
<223> OTHER INFORMATION: Description of Unknown Virus Organism:
      Artificial

<400> SEQUENCE: 14

His Gln Leu Ser Leu Pro Pro Pro Pro Pro His Gln Ser Thr Pro
  1               5                  10                  15
```

-continued

```
His Cys Ser Ser Asp Ser Thr Gly Leu Pro Pro Pro Pro Thr Ser Tyr
            20                  25                  30

Ser Ile Pro Ser Met Thr Leu Ser Pro Glu Pro Leu Pro Pro Pro Ala
        35                  40                  45

Ala Pro Ala His Pro Leu Pro Gly Val Ile Tyr Asp Gln Gln Ala Leu
    50                  55                  60

Pro Pro Thr Pro Gly Pro Pro Trp Trp Pro Pro Val Arg Asp Pro Thr
65                  70                  75                  80

Pro Thr Thr Gln Thr Pro Pro Thr Asn Thr Lys Gln Pro Gly Asp Gln
                85                  90                  95

Gly Gln Gly Arg Gly Arg Trp Arg Gly Arg Gly Arg Ser Lys Gly Arg
            100                 105                 110

Gly Arg Met His Lys Leu Pro Glu Pro Arg Arg Pro Gly Pro Asp Thr
        115                 120                 125

Ser Ser Pro Ser Met Pro Gln Leu Ser Pro Val Val Ser Leu His Gln
    130                 135                 140

Gly Gln Gly Pro Glu Asn Ser Pro Thr Pro Gly Pro Ser Thr Ala Gly
145                 150                 155                 160

Pro Val Cys Arg Val Thr Pro Ser Ala Thr Pro Asp Ile Ser Pro Ile
                165                 170                 175
```